US011266629B2

(12) United States Patent
Tumpowsky

(10) Patent No.: US 11,266,629 B2
(45) Date of Patent: Mar. 8, 2022

(54) MELANIN COMPOSITIONS AND DEVICES FOR PROTECTING TISSUES FROM RADIATION DAMAGE

(71) Applicant: Goodwin & Wells LLC, New York, NY (US)

(72) Inventor: Paul Tumpowsky, New York, NY (US)

(73) Assignee: Goodwin & Wells LLC, New York, NY (US)

( * ) Notice: Subject to any disclaimer, the term of this patent is extended or adjusted under 35 U.S.C. 154(b) by 163 days.

(21) Appl. No.: 15/584,179

(22) Filed: May 2, 2017

(65) Prior Publication Data

US 2017/0312250 A1 Nov. 2, 2017

Related U.S. Application Data

(60) Provisional application No. 62/330,435, filed on May 2, 2016.

(51) Int. Cl.

| | |
|---|---|
| ***A61K 31/405*** | (2006.01) |
| ***A61K 8/72*** | (2006.01) |
| ***A61K 9/00*** | (2006.01) |
| ***A61K 31/136*** | (2006.01) |
| ***A61M 31/00*** | (2006.01) |
| ***A61K 9/20*** | (2006.01) |

(52) U.S. Cl.

CPC .............. *A61K 31/405* (2013.01); *A61K 8/72* (2013.01); *A61K 9/0031* (2013.01); *A61K 9/0034* (2013.01); *A61K 9/20* (2013.01); *A61K 31/136* (2013.01); *A61M 31/00* (2013.01)

(58) Field of Classification Search

CPC ...... A61K 31/136; A61K 31/405; A61K 8/72; A61K 9/0031; A61K 9/0034; A61K 9/02; A61K 9/20; A61M 31/00

See application file for complete search history.

(56) References Cited

U.S. PATENT DOCUMENTS

| | | | | |
|---|---|---|---|---|
| 3,211,143 | A * | 10/1965 | Grossberg | A63B 71/085 |
| 5,112,883 | A | 5/1992 | Gallas | |
| 5,538,752 | A * | 7/1996 | Blanchette | A01N 63/30 427/4 |
| 5,703,051 | A | 12/1997 | Berliner et al. | |
| 5,888,645 | A | 3/1999 | Lindgaard et al. | |
| 6,525,019 | B2 | 2/2003 | D'amato | |
| 8,586,090 | B2 * | 11/2013 | Dadachova | A61K 9/0019 424/195.15 |
| 2002/0022758 | A1 | 2/2002 | Wolfson et al. | |
| 2009/0209852 | A1 * | 8/2009 | Mate | A61K 31/136 |
| 2011/0240040 | A1 * | 10/2011 | Westbrook | A61B 13/00 128/860 |
| 2013/0131427 | A1 | 5/2013 | Johnson et al. | |
| 2014/0037674 | A1 | 2/2014 | Dadachova et al. | |
| 2014/0048079 | A1 * | 2/2014 | Gardner | A61M 16/0497 |

FOREIGN PATENT DOCUMENTS

| | | |
|---|---|---|
| WO | WO 2008132732 | 11/2008 |

OTHER PUBLICATIONS

Schweitzer Melanins as Radioprotectors, PLoS ONE, September, p. 1 (Year: 2009).*

Basu Radiotherapy for oral cancers Review Article, S2 January, p. S72 (Year: 2012).*

Fesinmeyer, Megan Dann et al., "Effect of Radiotherapy Interruptions on Survival in Medicare Enrollees with Local and Regional Head-and-Neck Cancer," Int. J. Radiation Oncology Bio. Phys., vol. 78 No. 3, pp. 675-681, 2010, Elsevier.

Bhattasali, Onita et al., "Patient Reported Outcomes Following Stereotactic Body Radiation Therapy for Clinically Localized Prostate Cancer," Radiation Oncology, vol. 9 No. 52, 2014, BioMed Central.

Schweitzer, Andrew D. et al., "Melanin-covered Nanoparticles for Protection of Bone Marrow During Radiation Therapy of Cancer," Int. J. Radiation Oncology Bio. Phys., vol. 78 No 5, pp. 1494-1502, Dec. 2010, Elsevier.

Trotti, Andy et al., "Mucositis incidence, severity and associated outcomes in patients with head and neck cancer receiving radiotherapy with or without chemotherapy: a systematic literature review," Radiotherapy & Oncology, vol. 66, pp. 253-262, 2003, Elsevier.

Dadachova, Ekaterina et al., "The radioprotective properties of fungal melanin are a function of its chemical composition, stable radical presence and spatial arrangement," Pigment Cell Melanoma Res., vol. 21, pp. 192-199, Blackwell Munksgaard, 2007.

Elting, Linda S. et al., "Risk, Outcomes, and Costs of Radiation-Induced Oral Mucositis Among Patients with Head-and-Neck Malignancies," Int. J. Radiation Oncology Bio. Phys., vol. 68 No. 4, pp. 1110-1120, 2007, Elsevier.

International Search Report and Written Opinion in related application PCT/US2017/030525, dated Aug. 1, 2017, 8 pages.

* cited by examiner

*Primary Examiner* — Matthew P Coughlin
*Assistant Examiner* — Thurman Wheeler
(74) *Attorney, Agent, or Firm* — Amster, Rothstein & Ebenstein LLP

(57) ABSTRACT

Disclosed are melanin compositions and devices, and methods of use thereof, to protect internal tissues and organs from radiation damage and to prevent or alleviate negative side effects associated with radiation exposure.

17 Claims, No Drawings

# MELANIN COMPOSITIONS AND DEVICES FOR PROTECTING TISSUES FROM RADIATION DAMAGE

CROSS-REFERENCE TO RELATED APPLICATIONS

This application claims the benefit under 35 U.S.C. § 119(e) to U.S. Provisional Application No. 62/330,435, filed May 2, 2016, the entire contents of which are incorporated herein by reference in their entirety.

FIELD OF THE DISCLOSURE

Disclosed are compositions, devices and methods for using the radiation-absorbing properties of melanin to protect internal tissues and organs from radiation damage and to prevent or alleviate negative side effects associated with radiation exposure.

BACKGROUND OF THE DISCLOSURE

Exposure to radiation is associated with a number of complications that may compromise the health and quality of life of subjects exposed to radiation. For example, such exposure may be in connection with medical imaging or cancer treatment.

Head and neck cancers comprise up to 5% of all cancers in the US, with approximately 48,000 new diagnoses each year. Cancers of the head and neck are most commonly treated with radiotherapy, which can entail a number of complications that compromise patients' health and quality of life and affect their ability to complete planned cancer treatment. For some patients, complications can be so debilitating that they may tolerate only lower doses of therapy, postpone scheduled treatments, or discontinue treatment entirely. Oral complications can also lead to serious systemic infections. Examples of common side effects/complications due to radiotherapy are shown in Table 1.

TABLE 1

Examples of side effects of head and neck radiotherapy.

| | |
|---|---|
| Mucositis | inflammation and ulceration of the mucous membranes of the oral cavity (oral mucositis) and/or the gastrointestinal tract; can increase the risk for pain, oral and systemic infection, and nutritional compromise |
| Infection | viral, bacterial, and fungal; results from myelo-suppression, xerostomia, and/or damage to the mucosa from chemotherapy or radiotherapy |
| Xerostomia/ salivary gland dysfunction | dryness of the mouth due to thickened, reduced, or absent salivary flow; increases the risk of infection and compromises speaking, chewing, and swallowing. Medications other than chemotherapy can also cause salivary gland dysfunction. Persistent dry mouth increases the risk for dental caries. |
| Functional disabilities | impaired ability to eat, taste, swallow, and speak because of mucositis, dry mouth, trismus, and infection |
| Taste alterations | changes in taste perception of foods, ranging from unpleasant to tasteless |
| Nutritional compromise | poor nutrition from eating difficulties caused by mucositis, dry mouth, dysphagia, and loss of taste |
| Abnormal dental development | altered tooth development, craniofacial growth, or skeletal development in children secondary to radiotherapy and/or high doses of chemotherapy before age 9 |
| Dental decay | lifelong risk of rampant dental decay that may begin within 3 months of completing radiation treatment if changes in either the quality or quantity of saliva persist |
| Trismus/tissue fibrosis | loss of elasticity of masticatory muscles that restricts normal ability to open the mouth |
| Osteonecrosis | blood vessel compromise and necrosis of bone exposed to high-dose radiation therapy; results in decreased ability to heal if traumatized |

TABLE 1-continued

Examples of side effects of head and neck radiotherapy.

The majority of patients receiving radiation therapy for head and neck cancer are unable to continue eating by mouth due to oral mucositis pain and often receive nutrition through a gastrostomy tube or intravenous line. It has been demonstrated that patients with oral mucositis are significantly more likely to have severe pain and a weight loss of ≥5% (Int J Radiat Oncol Biol Phys. 68:4 (Jul. 15, 2007): 1110-20). In one study, approximately 16% of patients receiving radiation therapy for head and neck cancer were hospitalized due to mucositis. Further, 11% of the patients receiving radiation therapy for head and neck cancer had unplanned breaks in radiation therapy due to severe mucositis (Radiother Oncol. 2003 March; 66(3):253-262).

Radiation-induced oral mucositis also has a significant economic impact due to costs associated with pain management, liquid diet supplements, gastrostomy tube placement or total parenteral nutrition, management of secondary infections and hospitalizations. In one study of patients receiving radiation therapy for head and neck cancer, oral mucositis was associated with an increase in costs ranging from $1700-$6000 per patient, depending on the grade of oral mucositis (Int J Radiat Oncol Biol Phys. 68:4 (Jul. 15, 2007): 1110-20).

Rectal and prostate cancers represent some of the most common cancers in the US, with 39,090 and 220,800 estimated new cases in 2015, respectively. Patients with prostate or rectal cancer may receive radiation therapy as part of their treatment plan, and can often suffer debilitating side effects which may interfere with their treatment and reduce quality of life. Typical side effects include nausea and vomiting, diarrhea, rectal irritation, rectal skin changes, tiredness and sexual dysfunction (Radiat Oncol. 2014; 9:52).

In animal models, melanin has been demonstrated to protect biological tissue from radiation exposure (see Pigment Cell & Melanoma Research, April 2008, 21:192-199; Int J Radiat Oncol Biol Phys. 2010 Dec. 1; 78(5): 1494-1502; and U.S. Pat. No. 9,408,882 (which is incorporated by reference herein in its entirety)).

The compositions, devices and methods disclosed herein are based on melanin's radiation-absorbing properties and the use of melanin as a radio-protectant for healthy tissues during cancer radiotherapy, medical imaging and other radiation exposures.

BRIEF SUMMARY

Disclosed herein is a mouth insert device for use in a subject to protect the subject's head or neck tissues from one or more side effects associated with exposure of the head or neck tissues to radiation, wherein the mouth insert device comprises (i) an effective amount of melanin to protect the subject's head or neck tissues from one or more side effects associated with exposure of the tissues to radiation, and (ii) a size and shape compatible with insertion of the mouth insert device into the subject's oral cavity.

Disclosed herein is a method for alleviating or preventing one or more side effects associated with exposure of a subject's head and neck to radiation, the method comprising inserting one or more mouth insert devices into the subject's mouth during exposure of the subject's head, neck, or head and neck to radiation so as to protect one or more head and neck tissues from radiation exposure, wherein each mouth insert device comprises (i) an effective amount of melanin to protect the subject's head and neck tissue, and (ii) a size and shape compatible with insertion of the mouth insert device into the subject's oral cavity.

Disclosed herein is a suppository comprising melanin.

Disclosed herein is method for alleviating or preventing one or more side effects associated with exposure of a subject to radiation, the method comprising administering to the subject prior to radiation exposure a suppository comprising an effective amount of melanin to protect the subject's internal tissues.

DETAILED DESCRIPTION

Disclosed herein are melanin compositions, methods and devices to facilitate the presence of melanin in an area of the body exposed to radiation in order to protect local cells, tissues and organs from exposure during the course of the radiation event. The radiation-absorbing properties of melanin protects cells, tissues and organs from radiation damage and prevents or alleviates negative side effects associated with radiation exposure.

The term "effective amount" or "effective dose" as used herein means an amount of melanin sufficient to protect cells, tissues and organs from radiation exposure. An appropriate "effective amount" or "effective dose" in any individual case may be determined using standard techniques known in the art, such as a dose escalation study.

The term "protect" as used herein means alleviating, abating, ameliorating, relieving, reducing, inhibiting, preventing, or slowing at least one side effect of radiation exposure, preventing additional side effects of radiation exposure, reducing or slowing the progression of one or more side effects of radiation exposure, or causing regression of one or more side effects of radiation exposure. The methods, devices and compositions provided herein can be used in subjects that already exhibit one or more side effects of radiation exposure.

The term "compatible with" as used herein means, with respect to a device, having a size and shape not larger than the orifice into which the device is intended to be inserted and is capable of being inserted without causing serious injury or ongoing pain in the subject.

The term "pharmaceutical composition" as used herein refers to a composition comprising at least one active agent as described herein (such as, for example, melanin), or a combination of two or more active agents, and one or more other components suitable for use in pharmaceutical delivery such as carriers, stabilizers, diluents, dispersing agents, suspending agents, thickening agents, excipients, and the like.

The term "subject" as used herein encompasses mammals, including, but not limited to, humans, non-human primates, rodents (such as rats, mice and guinea pigs), and the like. In some embodiments, the subject is a human.

The melanin can be isolated, extracted, purified or derived from a melanin-containing biological source or synthesized chemically. Melanin can also be provided as a melanin-containing biological source, for example, as ground up melanin-containing mushrooms. Preferably, melanin comprises at least 10% of the dry weight of the biological source.

The biological source can be, for example, a melanin-containing plant, cell, fungus or microorganism such as a bacterium. Preferred fungi include melanin-containing edible mushrooms, such as *Auricolaria auricular*-judge or *Pleuroius cystidiosus*, and yeast such as *Cryptococcus neoformans*. In an embodiment, the melanin is in a composition substantially-free of fungal material or other non-melanin components of the biological source. In some embodiments, the melanin composition includes less than 1%, less than 2%, less than 3%, less than 4%, less than 5%, less than 10%, less than 15%, less than 20% or less than 25%, by dry weight, of non-melanin fungal material or other non-melanin components of the biological source. Other non-limiting examples of biological sources of melanin include the ink of squid, *Sepia* species, cuttlefish and cephalopod.

A chemical source for melanin can be auto- or catalytic-polymerization of certain phenolic compounds like L-dopa. The melanin can comprise allomelanin, pheomelanin and/or eumelanin. In some embodiments, the melanin is not in the form of melanized nanoparticles, melanin nanoshells and melanin-containing hollow spheres.

In some embodiments, an effective dose of melanin is an amount where the density of melanin is sufficient to leverage melanin's electron scattering and anti-oxidant properties without inducing excessive attenuation of radiation. For a suppository or mouth bar, effective doses can be determined as the total density of melanin in the path of incident beams of radiation. In some embodiments, the density of melanin embedded in the mouth insert device or applied to the mouth insert device is from about 0.01-0.05 $g/cm^3$, 0.05-0.1 $g/cm^3$ or >0.1 $g/cm^3$. In some embodiments, the thickness of melanin embedded in the mouth insert device or applied to the outside of the device is from about 0.05 mm-0.1 mm, 0.1 mm-0.5 mm, 0.5 mm-1 mm, 1 mm-5 mm, or >5 mm.

Disclosed herein is a mouth insert device, also referred to herein as a mouth bar or mouth guard, for use in a subject to protect the subject's head or neck tissues from one or more side effects associated with exposure of the head or neck tissues to radiation, wherein the mouth insert device comprises (i) an effective amount of melanin to protect the subject's head or neck tissues from one or more side effects associated with exposure of the tissues to radiation, and (ii) a size and shape compatible with insertion of the mouth insert device into the subject's oral cavity. The mouth insert device disclosed herein would limit the complications associated with radiotherapy for cancers of the head and neck and decrease mean interruption time, the average length of treatment pause during a course of radiotherapy. The melanin-containing mouth bar disclosed herein is inserted during radiation delivery to absorb off-target radiation and protect local tissues, for example, the oral mucosa and salivary glands.

A mouth insert device preferably has a size and shape compatible with insertion into a subject's oral cavity. In some embodiments, the mouth insert device is further compatible with one or more internal structures of the subject's oral cavity, such as the mouth, throat, cheeks, tongue and teeth. In some embodiments, the mouth guard is formed so that it encompasses the teeth and gums. In some embodiments, the mouth guard includes a strip that passes underneath the tongue. In some embodiments, the strip beneath the tongue may have small extrusions containing melanin or with melanin paste applied that can be positioned near the salivary glands. In some embodiments, melanin is embedded in or applied to the strip. In some embodiments the mouth guard includes a strip that passes above the tongue; melanin may be embedded in or applied to this strip. In some embodiments, the mouth guard covers the roof of the mouth.

A mouth insert device may be made of any suitable material. In some embodiments, the mouth insert device is made of plastic. In some embodiments, the material is soft, flexible, moldable or pliable or otherwise capable of being shaped to fit into a subject's oral cavity as desired. In some embodiments, the material is biocompatible, such as biocompatible plastic.

In some embodiments, the melanin is incorporated into or embedded in the material from which the mouth insert device is manufactured.

Disclosed herein is a method for alleviating or preventing one or more side effects associated with exposure of a subject's head and neck to radiation, the method comprising inserting one or more mouth insert devices into the subject's mouth during exposure of the subject's head, neck, or head and neck to radiation so as to protect one or more head and neck tissues from radiation exposure.

In some embodiments, the method further comprises applying a melanin composition to a surface of the mouth insert device prior to insertion of the mouth insert device into the subject's mouth. In some embodiments, the melanin composition is formulated as a slurry, gel or paste. In some embodiments, the melanin composition is a pharmaceutical composition that includes melanin. In some embodiments, a slurry, gel or paste contains from about 10% to about 90% water, by volume, and an effective amount of melanin.

In a non-limiting example of a mouth insert device disclosed herein, melanin or ground up mushrooms with high melanin content are placed in a suitable soft container to be held in the mouth only during irradiation of tumor sites. Reduction of side effects and mean interruption time results in improved treatment outcomes for patients, as patients with interruption of treatment show a 68% increase in risk of death as compared to patients without treatment interruption (Int. Journal of Radiation Oncol. Biology Physics. Volume 78, Issue 3, 1 Nov. 2010, Pages 675-681).

In another non-limiting example, melanin or ground up mushrooms with high melanin content in a suitable soft container that could be held in the mouth protect against head and neck radiation. In a further example, the melanin is contained in three small separate soft containers with one being held under the tongue to protect the major salivary gland there and two others close to the internal surface of each cheek. The methods disclosed herein may further comprise a melanin-containing gel, paste or slurry applied to the internal surfaces of the subject's mouth and/or throat concurrently with use of the mouth insert device(s) during the period of radiation exposure. Presence of melanin in the mouth would reduce local damage to salivary glands and reduce the likelihood of mucositis.

Disclosed herein is a suppository that includes melanin. In some embodiments, the suppository contains a pharmaceutical composition that includes melanin. In some embodiments, the melanin is applied to the outside of a suppository base. A melanin-containing suppository is used to protect local tissues from radiation exposure, for example, during a course of radiation therapy or medical imaging, or any other procedure where internal tissues are exposed to radiation. Accordingly, disclosed herein is a method for alleviating or preventing one or more side effects associated with exposure of a subject to radiation, the method comprising administering to the subject prior to radiation exposure a suppository comprising an effective amount of melanin to protect the subject's internal tissues from radiation exposure. In some embodiments, the suppository is a rectal suppository, a vaginal suppository or a urethral suppository.

In a non-limiting example, a suppository containing melanin is inserted into a patient prior to radiation treatment for prostate or rectal cancer. Melanin particles protect the tissues against radiation from focused radiation treatments locally in the areas of the rectum or prostate thus reducing negative side effects associated with radiation therapy.

Suppositories are solid dosage formulations intended for insertion into a body orifice other than the mouth, such as the rectum, vagina or urethra, where they melt, soften, or dissolve and exert local or systemic effects. The suppository can be used for routine use in oncology care to reduce side effects of normal courses of radiotherapy and in turn, improve patients' outcomes, and other procedures where radiation may affect local tissues in the area of the suppository.

Methods of making suppositories of typical sizes and shapes for various administration routes are known in the art. A typical suppository is conical or torpedo-shaped solid preparation containing one or more active agents (for example, melanin) and a base that enables the fabrication of a suppository which is relatively solid at room temperature and in a dry environment, but which melts at body temperature and in contact with body fluids so as to allow the active agent(s) to be brought in contact with the local tissue upon administration. In some embodiments, melanin is applied to or embedded in only the portion of the suppository reaching the lower rectum and anus; these would be placed far enough (e.g. >1 cm) from the path of radiation beams headed to the tumor that they would not cause. In embodiments where the melanin is placed distant form tumor, densities of melanin >5 gm/cm$^3$ may be tolerable. This is particularly desirable if the tumor is in the prostrate, as it permits using large amounts of radioprotective material to ensure maximum protection of normal tissue.

The suppository base typically comprises waxy materials in which the active agent has been dissolved or suspended. Non-limiting examples of base components include fatty acid monoglyceride, fatty acid diglyceride, fatty acid triglyceride, polyethylene glycol, glycerin, glyceryl monopalmitate, glyceryl monostearate, hydrogenated coconut oil fatty acids, cocoa butter, hydrogenated palm kernel oil fatty acids, and mixtures thereof, the base may also include additional substances such as water, a pH modifier, consistency agent, adjuvants, carriers, preservatives, vitamins, minerals, or other substances are well known to persons skilled in the art. The properties and ingredients of the suppository base can be adjusted to determine the desired consistency and dissolution time of the suppository.

Disclosed herein is a removable device for use in a subject to protect the subject's internal tissues from one or more side effects associated with exposure to radiation, wherein the removable device comprises (i) an effective amount of melanin to protect the subject's internal tissues from one or more side effects associated with exposure of the tissues to radiation, and (ii) a size and shape compatible with insertion of the removable device into the subject's rectum or vagina. The removable device will allow for precise melanin localization to protect local tissues in the area of the rectum or vagina. The removable device may be used for routine use in oncology care to reduce side effects of normal courses of radiotherapy and in turn, improve patients' outcomes, and other procedures where radiation may affect local tissues in the area of the vagina, prostate and rectum. Accordingly, disclosed herein is a method for alleviating or preventing one or more side effects associated with exposure of a one or more internal tissues of a subject to radiation, the method comprising inserting a removable device into the subject's vagina, or rectum, or vagina and rectum during exposure of the internal tissues in the area of the subject's vagina, or rectum, or vagina and rectum to radiation so as to protect one or more internal tissues from radiation exposure.

A removable device preferably has a size and shape compatible with insertion into a subject's vagina or rectum.

A removable device may be made of any suitable material. In some embodiments, the removable device is made of plastic. In some embodiments, the material is soft, flexible, moldable or pliable or otherwise capable of being shaped to fit into a subject's vagina or rectum. In some embodiments, the material is biocompatible, such as biocompatible plastic.

In some embodiments, the melanin is incorporated into or embedded in the material from which the removable device is manufactured.

In some embodiments, the method further comprises applying a melanin composition, for example a pharmaceutical composition, to a surface of removable device prior to insertion of the removable device into the subject's vagina or anus. In some embodiments, the melanin composition is formulated as a slurry, gel or paste. In some embodiments, a slurry, gel or paste contains from about 10% to about 90% water, by volume, and an effective amount of melanin.

The radiation can comprise ionizing radiation. The radiation can be, for example, gamma radiation, x-ray radiation, bremsstrahlung radiation, ultraviolet radiation, and particulate radiation (e.g., $\alpha$-radiation and $\beta$-radiation). The source of the radiation can be a medical isotope. For example, the source of the radiation can be radiation therapy used for treatment of disease (such as radiotherapy), radiation from a medical imaging device (such as a CT scanner) or radiation used for radiation surgery (e.g. stereotactic radiation surgery).

In some embodiments, the subject has been, is being, or will be exposed to a single radiation exposure of 10 mGy, 20 mGy, 50 mGy, 100 mGy, 500 mGy, 1 Gy, 1.5 Gy, 2 Gy or greater, 5 Gy or greater, 7.5 Gy or greater, 10 Gy or greater or greater than 10 Gy. In humans, a whole-body exposure to 5 or more Gy of high-energy radiation at one time usually leads to death within 14 days.

Preferably, one or more internal tissues or organs are protected by melanin. In some embodiments the one or more internal tissues are selected from the group consisting of: gastrointestinal tract, mouth, salivary glands, teeth, tongue, throat, esophagus, stomach, large intestine, small intestine, prostate, urethra, vagina, anus and rectum.

Preferably, one or more side effects of radiation exposure are alleviated or prevented by the melanin devices, compositions and methods disclosed herein. In some embodiments, the one or more side effects are selected from the group consisting of: nausea, vomiting, diarrhea, rectal irritation, rectal skin changes, oral mucositis, infection, xerostomia, salivary gland dysfunction, impaired ability to eat, taste, swallow, and speak, taste alterations, nutritional compromise, abnormal dental development, trismus/tissue fibrosis, osteonecrosis, tiredness and sexual dysfunction.

All patent applications, patents and other publications cited herein are incorporated by reference in their entirety. One or more embodiments of the present invention have been described. Nevertheless, it will be understood that various modifications may be made without departing from the spirit and scope of the invention. Accordingly, other embodiments are within the scope of the following claims.

What is claimed is:

1. A mouth insert device for use in a subject to protect the subject's head or neck tissues from one or more side effects associated with exposure of the head or neck tissues to ionizing radiation, wherein the mouth insert device comprises (i) an amount of melanin effective to protect the subject's head or neck tissues from one or more side effects associated with exposure of the tissues to ionizing radiation, and (ii) a size and shape compatible with insertion of the mouth insert device into the subject's oral cavity, and with absorbance of off-target radiation, and wherein (iii) the mouth insert device is pliable so as to fit the subject's oral cavity, wherein the amount of melanin does not comprise melanin nanoshells, melanized nanoparticles, or melanin-containing hollow spheres, and wherein the device comprises a density of melanin of from 0.01 to 0.05 g/cm$^3$.

2. The mouth insert device of claim 1, wherein the size and shape of the mouth device is further compatible with one or more internal structures of the subject's oral cavity.

3. The mouth insert device of claim 2, wherein the one or more internal structures of the subject's oral cavity are selected from the group consisting of: mouth, throat, cheeks, tongue and teeth.

4. The mouth insert device of claim 1, wherein the mouth insert device is made of plastic.

5. The mouth insert device of claim 4, wherein the plastic is biocompatible.

6. The mouth insert device of claim 4, wherein the melanin is incorporated into the material from which the mouth insert device is manufactured.

7. The mouth insert device of claim 1, wherein the melanin comprises melanin from a biological source.

8. The mouth insert device of claim 1, wherein the ionizing radiation is gamma radiation or X-ray radiation.

9. A method for alleviating or preventing one or more side effects associated with exposure of a subject's head and neck to ionizing radiation, the method comprising inserting one or more mouth insert devices of claim 1 into the subject's mouth during exposure of the subject's head, neck, or head and neck to radiation so as to protect one or more head and neck tissues from radiation exposure, wherein each mouth insert device comprises (i) an amount of melanin effective to protect the subject's head and neck against ionizing radiation, and (ii) a size and shape compatible with insertion of the mouth insert device into the subject's oral cavity.

10. The method of claim 9, wherein the one or more head and neck tissues are selected from the group consisting of: oral tissue, salivary glands, tongue, teeth and throat.

11. The method of claim 9, wherein the size and shape of the mouth device is further compatible with one or more internal structures of the subject's oral cavity.

12. The method of claim 11, wherein the one or more internal structures of the subject's oral cavity are selected from the group consisting of: mouth, throat, cheeks, tongue and teeth.

13. The method of claim 9, wherein the melanin comprises melanin from biological source.

14. The method of claim 9, further comprising wherein a melanin composition has been applied to a surface of the mouth insert device prior to insertion of the mouth insert.

15. The method of claim 14, wherein the melanin composition is formulated as a slurry, gel or paste.

16. The method of claim 9, wherein the one or more side effects are selected from the group consisting of: oral mucositis, infection, xerostomia, salivary gland dysfunction, impaired ability to eat, ability to taste, ability to swallow, ability to speak, taste alterations, nutritional compromise, abnormal dental development, trismus/tissue fibrosis and osteonecrosis.

17. The device of claim 1, wherein the size and shape protect a salivary gland under the tongue and/or close to a cheek from external ionizing radiation when inserted in a subject's mouth.

* * * * *